(12) United States Patent
Riesinger

(10) Patent No.: US 9,707,311 B2
(45) Date of Patent: Jul. 18, 2017

(54) WOUND CARE ARTICLE HAVING AN ABSORBENT SHELL

(75) Inventor: Birgit Riesinger, Ostbevern (DE)

(73) Assignee: BSN MEDICAL, GMBH, Hamburg (DE)

( * ) Notice: Subject to any disclaimer, the term of this patent is extended or adjusted under 35 U.S.C. 154(b) by 1250 days.

(21) Appl. No.: 12/672,011

(22) PCT Filed: Aug. 1, 2008

(86) PCT No.: PCT/EP2008/060165
§ 371 (c)(1),
(2), (4) Date: Dec. 29, 2011

(87) PCT Pub. No.: WO2009/019224
PCT Pub. Date: Feb. 12, 2009

(65) Prior Publication Data
US 2012/0095419 A1    Apr. 19, 2012

(30) Foreign Application Priority Data
Aug. 3, 2007   (DE) .......................... 10 2007 036 758

(51) Int. Cl.
*A61M 1/00* (2006.01)
*A61L 15/60* (2006.01)
(Continued)

(52) U.S. Cl.
CPC ........ *A61L 15/60* (2013.01); *A61F 13/00029* (2013.01); *A61F 13/00063* (2013.01);
(Continued)

(58) Field of Classification Search
CPC ............... A61L 15/60; A61F 13/00029; A61F 13/00063; A61F 13/00068; A61F 13/00072; A61F 13/00; A61F 2013/00093; A61F 2013/00106; A61F 2013/00153; A61F 2013/00174; A61F 2013/00268; A61F 2013/00412; A61F 2013/00463;
(Continued)

(56) References Cited

U.S. PATENT DOCUMENTS 3,670,731 A    6/1972   Harmon
4,056,103 A    11/1977  Kaczmarzyk et al.
(Continued)

FOREIGN PATENT DOCUMENTS

DE    10059439    8/2001
DE    2021695     1/2003
(Continued)

OTHER PUBLICATIONS

Definition of "Fleece" http://www.merriam-webster.com/dictionary/fleece.
(Continued)

*Primary Examiner* — Philip R Wiest
(74) *Attorney, Agent, or Firm* — David G. Rosenbaum; J. Peter Paredes; Rosenbaum IP, P.C.

(57) ABSTRACT

The invention relates to a wound care article (100; 200; 300; 400; 500) comprising at least one body (1; 11; 21) absorbing the liquid wound exudates, and at least one shell (2; 12; 22) at least partially encompassing the body (1; 11; 21). The shell (2; 12; 22) itself is designed to absorb fluids.

23 Claims, 7 Drawing Sheets

Figure 1:
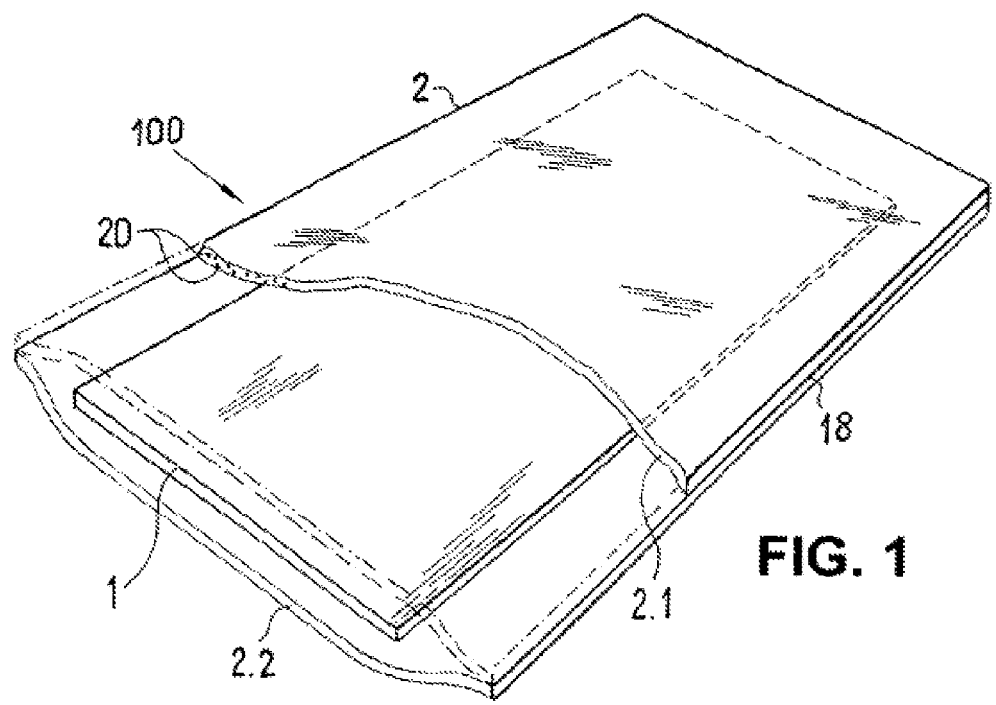

(51) Int. Cl.
*A61F 13/00* (2006.01)
*A61F 17/00* (2006.01)

(52) U.S. Cl.
CPC .. *A61F 13/00068* (2013.01); *A61F 13/00072* (2013.01); *A61F 17/00* (2013.01); *A61F 2013/0054* (2013.01); *A61F 2013/0057* (2013.01); *A61F 2013/0074* (2013.01); *A61F 2013/0091* (2013.01); *A61F 2013/00093* (2013.01); *A61F 2013/00106* (2013.01); *A61F 2013/00153* (2013.01); *A61F 2013/00174* (2013.01); *A61F 2013/00268* (2013.01); *A61F 2013/00412* (2013.01); *A61F 2013/00463* (2013.01); *A61F 2013/00536* (2013.01); *A61F 2013/00748* (2013.01); *A61F 2013/00897* (2013.01)

(58) Field of Classification Search
CPC .... A61F 2013/00536; A61F 2013/0054; A61F 2013/0057; A61F 2013/0074; A61F 2013/00748; A61F 2013/00897; A61F 2013/0091
USPC ............... 604/319, 358–384, 385.01, 385.04
See application file for complete search history.

(56) References Cited

U.S. PATENT DOCUMENTS

| | | | | |
|---|---|---|---|---|
| 4,335,722 | A | * | 6/1982 | Jackson .............. A61F 13/2051 604/364 |
| 4,616,644 | A | | 10/1986 | Saferstein et al. |
| 5,387,207 | A | | 2/1995 | Dyer et al. |
| 5,994,613 | A | * | 11/1999 | Cummings et al. ............ 602/58 |
| 6,103,358 | A | * | 8/2000 | Bruggemann et al. .... 428/317.9 |
| 6,967,261 | B1 | | 11/2005 | Soerens et al. |
| 7,959,624 | B2 | | 6/2011 | Riesinger |
| 2001/0024716 | A1 | | 9/2001 | Chen et al. |
| 2003/0113507 | A1 | * | 6/2003 | Niemeyer et al. .............. 428/77 |
| 2005/0143697 | A1 | * | 6/2005 | Riesinger ..................... 604/367 |
| 2005/0228350 | A1 | | 10/2005 | Ranganathan et al. |
| 2006/0025740 | A1 | | 2/2006 | Osborn, III et al. |
| 2006/0094997 | A1 | | 5/2006 | Kurata |
| 2009/0093779 | A1 | | 4/2009 | Riesinger |
| 2011/0171283 | A1 | | 7/2011 | Riesinger |
| 2011/0172617 | A1 | | 7/2011 | Riesinger |

FOREIGN PATENT DOCUMENTS

| | | |
|---|---|---|
| DE | 202 12 095 U1 | 2/2003 |
| DE | 60009079 T2 | 9/2004 |
| DE | 202004017052 | 7/2005 |
| DE | 202004018245 | 7/2005 |
| DE | 202006005966 | 10/2006 |
| DE | 102006031418 A1 | 1/2007 |
| DE | 102006017194 | 10/2007 |
| DE | 102007030931 | 1/2009 |
| EP | 0414541 A | 2/1991 |
| EP | 1374816 A2 | 1/2004 |
| EP | 0847260 B1 | 3/2007 |
| EP | 1860215 A | 11/2007 |
| GB | 978713 A | 12/1964 |
| GB | 983576 A | 2/1965 |
| WO | 93/15702 | 8/1993 |
| WO | WO-97/11658 A1 | 4/1997 |
| WO | WO-9728832 A | 8/1997 |
| WO | WO-9959647 A | 11/1999 |
| WO | WO 01/15644 A1 | 3/2001 |
| WO | 01/52780 | 7/2001 |
| WO | 03/094813 | 11/2003 |
| WO | WO-2004035668 A | 4/2004 |
| WO | 2006/020213 | 2/2006 |
| WO | 2006/048246 | 5/2006 |
| WO | WO-2006089551 A | 8/2006 |
| WO | 2007/051599 | 10/2007 |
| WO | 2007/118636 | 10/2007 |

OTHER PUBLICATIONS

Definition of "Mat" http://www.merriam-webster.com/dictionary/mat.

* cited by examiner

WOUND CARE ARTICLE HAVING AN ABSORBENT SHELL

CROSS-REFERENCE TO RELATED APPLICATIONS

This application is the National Stage of International Application No. PCT/EP2008/060165, filed on Aug. 1, 2008, which claims the benefit of German Application Serial No. 10-2007 036 758.0, filed on Aug. 3, 2007. The contents of both of the foregoing applications are hereby incorporated by reference in their entirety.

The invention concerns a wound care article consisting of at least one body absorbing the liquid wound exudates and at least one shell at least partially encompassing the body.

Exudates are liquids derived from blood plasma by means of the inflammation processes of the wound edema. Just as blood is responsible for the transport of nutrients and other courier materials, which supply the various parts of the body, the exudates similarly supply materials to the wound and to the healing processes operating there. In order to handle these multiple functions, they contain a broad spectrum of components with a specific gravity slightly higher than that of water. This differentiates it from transudate, which derives more likely from non-inflammatory processes and which has a lower specific gravity with a lower content of cell and protein material. In addition to supplying nutrients to the fibroblasts and the epithelial cells, the exudates coordinate the various processes of wound healing in a temporal and spatial sense by the high content of growth factors and cytokines. They are provided primarily by thrombocytes, keratinocytes, macrophages and fibroblasts. They modify the motility, migration and proliferation of the various cells involved in wound healing. Thus, the insertion of cells to the base of the wound is aided just as much as the supply of the newly formed granulation tissue by angiogenesis. The exudates also support wound cleaning. Exudates contain various serine proteases, cysteine proteases, and aspartate proteases as well as matrix metalloproteases, which concentrate on processing irreversibly damaged tissue and thus prepare the wound base for the subsequent phases of the healing process.

The physiological exudates contain in particular salts, glucose, cytokine and growth factors, plasma proteins, proteases (specifically matrix metalloproteases), granulocytes and macrophages.

If there is no significant progression of wound healing within a few weeks following the several phases of the wound healing process, the situation will be described as a chronic wound. In that context, the extended phase of exudation will be viewed as a complication and will be described as pathological exudation, which may contribute to turn the wound chronic. The underlying causes are generally complex and may well be also of a systemic nature. However, given the significance of the exudates for wound healing as described above, it is not a surprise that complications in the healing process will be reflected in a significantly changed composition and effect of the exudates.

Caused, among other reasons, by a change in the concentration of the various components of the exudates, the exudates lose their positive effect, which normally aids healing, in the presence of chronic wounds. In particular, the proportion of inflammatory cytokines and proteases is significantly higher in pathological exudates. In contrast, the proportion of growth factors is reduced. A particularly significant difference applies to the activity of the matrix metalloproteases discussed above. In addition to preparing the wound bed, they also participate in the subsequent restructuring of the granulation tissue to scar tissue. These enzymes are normally formed as an inactive pre-enzyme and are regulated in their activation by specific inhibitors (tissue inhibitors of metalloproteases, TIMPs), which simultaneously have a positive influence of cell growth rates themselves. It appears that disturbances in this regulatory system increase the activity of the proteases, which may contribute to active wound regression. Effects of the pathological exudates. With respect to the proportions of its components, the pathological exudates have lost the equilibrium that was beneficial to wound progression. This gives rise to several complications that lead to further deterioration of the wound and that turn it chronic.

1. Slower cell proliferation: The constituents of the physiological exudates support the proliferation of the various cell types required for proper healing. Pathological exudates are not able to do likewise.
2. Active damage to the wound perimeter: Skin surrounding the wound and not directly damaged will be damaged by the physiological exudates, such that the wound is enlarged.
3. Degradation of the fibronectins: Fibronectins, which are vital for the interaction of many cells with their surroundings, are degraded in the pathological exudates. As a result, the repair function of the fibroblasts, which is vital for the progression of the healing process, will be degraded.
4. Modified mitosis of the fibroblasts: Cell division of the fibroblasts will be degraded by the pathological exudates. In lieu of the normally present mitotically competent cells, there will be dormant cells, which may be due to a lack of relevant growth factors.

In light of the damaging effects imposed by the pathological exudates on the wound, which advance the process of chronification, the removal of the pathological exudates is normally a prerequisite for a progression of the wound status. Products for this purpose are known from the state of the art.

Thus, DE 10059439 and WO03094813 of the applicant of the present invention describe a wound cover for the absorption of wound exudates that contains superabsorbent polymers ("super absorber") and that exhibits outstanding properties regarding the absorption of wound exudates. It has been found that the use of said wound cover will significantly advance the healing process of chronically exuding wounds, such as in ulcus cruris. The teaching of DE 10059439 and of WO03094813 shall be added in full to the disclosure content of the present description.

The known wound care articles, designated as absorption bodies, are a wound cover, where the shell merely redirects wound liquids into the absorbent body contained by the shell. It has been found in many instances, particularly for strongly exudative wounds, that the absorption capacity of the wound cover is insufficient.

The invention has the objective of describing an improved wound care article of the same type, which is suitable in particular for strongly and very strongly exudative wounds. The wound care article should find applications for wide wounds as well as deep wounds, such as cavities.

It is a further objective of the present invention to generate a wound care article with a relatively larger proportion of actively absorbing area relatively to its entire area.

These objectives are achieved by the characteristics of the present set of claims. The dependent claims present advantageous embodiments. It should be noted here that the listed coverage data in each case include the respective extreme values.

The invention provides for a wound care article of the type describe above, where the shell itself can absorb liquids. Given that the shell itself can absorb significant amounts of wound liquids, the entire absorption capacity of the wound care article is increased. In addition, the absorbing function is brought into the closest possible proximity of the wound.

Moreover, the shell may also be designed with a lower absorption capacity than the absorbent body contained by the shell, where the shell may be designed with a lower proportion of absorbent substances or mixed with other absorbent materials.

This approach guarantees that the shell will always be dry to the touch due to its reduced absorbing capacity. Moreover, the shell will thus have a lower retention and consequently a higher liquid-releasing effect.

A preferred embodiment provides here that the wound cover will also have a sleeve at least partly surrounding the body absorbing wound liquids, which does not itself absorb liquids, and which
  a) acts as a wound separation screen, or which
  b) provides a function in protecting clothing.

The absorbent shell and the non-absorbent shell may be components of the overall shell here. Thus, for example,
  a) the non-absorbent shell may serve as the lower side (thus the side closest to the wound) of the overall shell, and the absorbent shell as the upper side (thus furthest away from the wound) of the overall shell, or
  b) the non-absorbent shell may serve as the upper side of the overall shell and the absorbent shell as the lower side of the overall shell.

Option a) is of particular interest, if the non-absorbent shell is a wound spacing screen.

A wound spacing screen is known, for example, from DE 102006017194 of the applicant of the present invention, the teaching of which is referenced here in full. Such a screen may consist, for example, of a material segment consisting of thermoblast with a first smooth surface and a second surface opposite the smooth surface with a plurality of three-dimensional perforations with walls emanating from the first smooth surface in each case extending beyond the edge with a free edge, such that the second surface is rough.

The perforations will be produced, for example, in a thermally assisted vacuum process with the assistance of a perforated screen attached to a drum. As a result, the finished foil material has a smooth surface and a rough surface formed by the angled walls of the perforations.

The flat side of the wound spacing screen rests either on the level area between the holes of the smooth surface or on the rough margins of the perforations, because the transition from the screen material to the perforations comprises the support area of the rough surface. As a result, the wound spacing screen may contact the wound in two ways with two very different functions.

An application with the smooth surface is particularly advantageous, because it determines the characteristic of the wound spacing screen as an non-traumatic wound cover inasmuch as it can be removed from the wound surface without leading to bleeding, pain or removal processes on conglutinated surfaces.

The angled segments on the rough surface lead to a reduction in the back-flow of wound liquids that previously moved through the wound spacing screen, thus contributing to keeping the wound dry.

The use of the wound spacing screen also keeps the micro-perforated surfaces of the body absorbing interior wound liquids clean, because solid contaminants, such as fibrinous membranes, encrustations or putrid processes, do not move to the interior, but remain in the wound base. This effect maintains the absorbing function of the body in the absorption of wound liquids, if the wound is contaminated, and extends its application duration or facilitates the initiation of this function, because said contaminants are retained on the surface of the wound spacing screen without closing the perforations.

The angled segments on the rough surface lead to a desirable reduction in the back-flow of wound liquids that penetrated previously.

The application with the rough side towards the wound causes the wound spacing screen to actively scrape the wound during movement, which facilitates exudation and thus flushing out pathogens etc., and also exerts a desirable tactical stimulation to tissue formation.

Option b) is of particular interest, if the non-absorbent shell fulfills the function of protecting clothing.

This often involves a sheet of water-impermeable material that is often laminated onto the shell. Said protector of clothing is often marked in color, such as in green in order to assure that the proper side is applied facing the wound.

Despite the high absorption capacity for liquids, it cannot be ruled out in some cases that absorbed exudates will be emitted from the body absorbing wound exudates, possibly even from the wound care article altogether. This may be unpleasant for the patient, because the exudates may be colored or may have an unpleasant odor, and it may represent a danger to the environment, specifically if the exudates are contaminated with pathogenic agents. In these cases, the protection of clothing as discussed above is primary.

However, it is also feasible to place a non-absorbent shell around the absorbent shell, i.e. to form a shell around the absorbent shell.

A preferred embodiment provides here that the wound cover will also have a sleeve at least partly surrounding the body absorbing wound liquids, which does not itself absorb liquids, and which
  a) acts as a wound separation cage, or which
  b) provides a function in protecting clothing.

The absorbent shell and the non-absorbent shell may be components of the overall shell here. In this embodiment, the outer shell may consist totally of said wound spacing screen, or the lower side (i.e. the side closest to the wound) of the outer shell acts as a wound spacing screen and the upper side (the side furthest from the wound) provides the protection for clothing.

The shell absorbing liquids may be closed or open. The shell should be interpreted to be a flat, prismatic, cylindrical, spherical or torus-shaped hollow body, which consists of a highly absorbent material, such as carboxymethylcellulose. It will be assumed that the highly absorbent material as defined in the present invention will be a material with an absorption potential for wound exudates that is at least triple the weight of the material.

Such highly absorbent materials are also labeled as "hydroactive polymers." In the following, this should be interpreted to refer to polymers. which have a high absorptive capacity for water, on the one hand, and which are capable of avoiding atmospheric release of liquids, on the other hand. Among others, this includes
  open-cell foams of polyurethane
  mats, sheets or fleeces of alginates mats, sheets or fleeces of carboxymethylcellulose, specifically sodium carboxymethylcellulose Alginates are derived from Phaeophyceae algae and processed to a fibrous fleece. In chemical terms, this is a polysaccharide, specifically the calcium and/or sodium salts of the alginic acid. Alginates can take up liquids up to 20 times their own weight, where the wound exudates are stored in the cavities. The $Ca^{2+}$ ions are exchanged against the $Na^+$ ions from the exudates, until the maximum saturation of Na ions in the alginates is reached. This process leads to an expansion of the wound cover and a modification of the alginate fiber into a gel body by expansion of the fibers.

Carboxymethylcellulose is available specifically in the form of sodium carboxymethylcellulose and is available commercially with the trade name "Hydrofaser." Hygienic and wound products modify the fibers to an extended flat matrix. Absorption of liquids from the wound exudates modifies the fibers gradually to a gel pillow, which holds the liquid and does not release it. In this process, the fibers are structured such that the wound exudates are absorbed only in a vertical direction. This implies that the exudates will not flow across the wound margin, if full capacity has not been reached. This effectively precludes maceration of the wound margin.

However, it is particularly advantageous to use superabsorbent polymers as the hydroactive polymers.

Superabsorbent polymers (SAP) are man-made compounds that are capable of absorbing a multiple of their weight—up to 1,000 times their weight. In chemical terms, they are a copolymer of acrylic acid (propene acid, $C_3H_4O_2$) and sodium acrylate (sodium salt of acrylic acid, $NaC_3H_3O_2$), where the ratio of the two monomers may vary. In addition, a so-called Core-Cross-Linker (CXL) is added to the monomer solution, which links the long-chain polymer molecules, which were formed, in certain places by chemical bridges ("networking" them). These bridges turn the polymer insoluble in water. When water or watery salt solutions enter the polymer particle, it expands and creates tension in the network on a molecular level, such that the water cannot escape again without outside assistance.

The superabsorbent polymers (SAP) in particular may be present in the form of an aggregation, where the term "aggregation" may include granules and powder as well as larger solids, such as foam structures. The material may also be cut or punched out of known Airlaid mats. Experiments have shown that material pieces obtained by cutting or punching (scraps) may speed up the rate of absorption by roughly 15% to 17%, compared to solid material of the same weight.

The hydroactive effect can be improved by thickeners. They include in particular alginic acid (E 400), agar (E 406), carrageen (E 407), carob meal (E 410), guar flour (E 412), tragacanth (E 413), gum arabic (E 414), xanthane (E 415), karaya gum (E 416), tara flour (E 417), Gellan (E 418), pectin (E 440), cellulose (E 460), cellulose ether, carboxymethylcellulose (E 466), hydroxypropylcellulose (E 463), hydroxypropylmethylcellulose (E 464), methylcellulose (E 461), methylethylcellulose (E 465), modified starch (group: E 1404, E 1410, E 1412, E 1413, E 1414, E 1420, E 1422, E 1440, E 1442, E 1450, E 1451).

The absorbing body may consist of at least one mat containing cellulose, such as of the type Airlaid, which will preferably be loose within the shell. Preferably, the mat will have a smaller area than the shell, if the latter is flat. The mat may consist of foam, such as polyurethane foam, which has particularly open cells.

It is particularly advantageous that the absorbing materials, specifically the superabsorbent polymers, are embodied as granules, powder, aggregation, compressed body, foam, fibers, woven fiber, fiber mat or fiber fleece and/or fiber padding.

The granular or powder form has been particularly advantageous and is preferred for that reason, as it may be incorporated easily in a fleece of fibrous material. This refers in particular to a so-called Airlaid mat.

An aggregation may consist in particular of small pieces of cut-up foam, specifically PU foam.

This may be cut up or punched out as well to form so-called scraps with similar advantages as described above.

Likewise, particularly for superabsorbent polymers, the fiber form is particularly preferred, because it is a very soft product in dry and in wet condition, which can be shaped easily, which is not stiff, and which moreover has low abrasion compared to the granular or powder superabsorbent polymers. This applies to fibers as such just as for woven fiber, fiber mat or fiber fleeces and/or fiber padding.

Said properties make the superabsorbent polymers in fiber form particularly suitable for products embodying the invention, which may be embodied as anal tampons, wound fillers, and cavity tampons. These applications require particularly soft materials.

Moreover, superabsorbent polymers in fiber form may exhibit or support a wick effect, which facilitates the removal of exudates from said wounds.

Furthermore, the applicant has noted that superabsorbent polymers in fiber form react faster to liquids than superabsorbent polymers in granular or powder form.

The absorbing body will preferably have an area-specific weight of 100 $g/m^2$-600 $g/m^2$, where the proportion of hydroactive and specifically superabsorbent polymers will be in the range of 25-100% by weight.

Suitable material for the shell includes renewable resources, such as wool, cotton, silk, spider silk (including recombinant), viscose or natural sponge. Furthermore, the shell may also consist of polymer-based synthetic soft foam, specifically polyurethane foam. It is conceivable here to produce the shell of solid foam by varying the density of the foam across the cross section of the mat. The material for the shell may be supplied in a sandwich structure. Reference is made here to the known Airlaid mat with perforated covers, where the mat will have at least a flexible, preferably pleated or crinkled cover.

A sandwich arrangement of the shell material may contain at least one foam layer and at least one foil-like or web-like cover layer, which may also be pleated or crinkled. The cover may also be embodied as textile material, whether woven or fleece.

The shell material may incorporate at least one super absorbent substance, which may be present likewise as a powder, granules or fibers.

The area or point linkage between the cover layer and the absorbent body is preferably embodied by gluing, welding, seams, quilting, bonding points, embossing or by thermomechanical linkages.

Glues may be used as spread or in spots with physiologically acceptable glues, such as starch glue, albumen glue, acrylate glue and the like.

Quilting seams may use elastic thread. This would facilitate an expansion of the absorbent body, if it takes up liquids.

Said bonding points are points pressed onto the wound care article, which facilitate a thermal and/or physical linkage of the various layers of the wound care article. Bonding points are normally spaced in a regular pattern.

Embossing refers to linkages generated merely by the exertion of pressure.

The term "thermo-mechanical linkages" is used hereinafter for linkages generated by exertion of pressure and heat. This may result specifically in a honeycombed, lozenge-shaped or checkered design in the presence of quilting seams, embossing or thermo-mechanical linkages.

If the proportion of superabsorbent polymers is very high, it may be infeasible to use bonding points for linkage with a potential cover made of cellulose. It may be necessary in such instance to link the two layers with an adhesive.

Other Designs

It is desirable in this connection to design the wound care article to include a nutrient, but at least a disinfectant or decontaminant and/or at least one agent and/or combination of agents to counteract proteases.

The disinfectant and/or combination of agents may be a combination of at least one vitamin or vitamin derivative, a metal ion, and a detergent. Alternatively, this may be a bacteriocin like inhibitory substance (BLIS) or a laminated magnetic particle, such as a silver donor, i.e. a silver ion.

The nutrient and/or combination of agents may be a combination containing at least the components of an enteric or para-oral dietary foodstuff. Alternatively, it may contain at least one agent of the group containing insulin, recombinant insulin, pro-insulin, an insulin-like growth factor (IGF), an insulin mimetic and/or a diabetic-specific energy supplier not based on glucose or sucrose.

The protease inhibiting agent and/or combination of agents may include at least one agent from the group containing protease inhibitors, superabsorbent polymers, chelating agents for bivalent cations, collagen, laminated magnetic particles, acids, buffers, non-pathogenic acid-producing microorganisms, probiotics and/or symbiotics.

In addition, the compound may also contain analgesic, i.e. pain-reducing agents. This refers primarily to all agents listed in Main Group 5 of the so-called "Red List." Particularly preferred are here anti-inflammatory agents such as the so-called cox inhibitors or the non steroidal anti-inflammatory drugs (NSAID), such as derivatives of propionic acid such as Naproxen, Ibuprofen, Ketoprofen, Fenoprofen, Flurbiprofen, Dexibuprofen or Tiaprofen acid, derivatives of acetic acid such as Diclofenac, Alclofenac, Fenclofenac, Etodolac, Aceclofenac, Sulindac or Indometacin, pyrrole acetic acids such as Ketorolac or Tolmetin, N-phenyl acetic acids such as Mefenamin acid or Flufenamin acid, salicylates such as acetyl salicylic acid, salicylic acid or Diffunisal, derivatives of Pyrazolon such as phenylbutazone, derivatives of Oxicam such as Piroxicam, Tenooxicam, Meloxicam or Lornoxicam, derivatives of enol acid such as Aminopyren or Antipyren, phenols such as Acetaminophen and the like. Additional compounds include COX-2 inhibitors such as Rofecoxib, Lumiracoxib or Celecoxib.

Moreover, the analgesic agents may include agents other than anti-inflammatory agents, such as opiates, local anesthetics such as Lidocain, Mepivacain, Prilocain, Procain, Syntocain, Tetracain, Gingicain, Articain, Bupivacain, Butanilicain, Chloroprocain, or, for example, Polidocanol.

Furthermore, the compound may also include anti-inflammatory agents that could have a secondary effect as analgesics other than the analgesics listed above, which may in part have anti-inflammatory effects, such as hormones, specifically Cortison and corticoids, such as glucocorticoids (e.g. Cortison, Cloprednol, Prednison, Prednisolon, Methylprednisolon, Deflazacort, Fluocortolon, Triamcinolon, Dexamethason, Betamethason) and mineralcorticoids (e.g. Aldosteron, Desoxycorticosteron, Fludrocortison).

Other relationships and background information regarding the nutrient, disinfecting or decontaminating and/or protease inhibiting agents and/or combination of agents are described in DE 102007030931 of the applicant of the present application, the content of which is referenced here in full. DE 102007030931 also describes other nutrient, disinfecting or decontaminating and/or protease inhibiting agents and/or compounds of agents that are also to be treated as published in this application.

Furthermore, the wound care article of the present invention may also be incorporated into a wound care system with wound drainage using a partial vacuum. Such systems are shown, for example, in the publications DE 202004017052, WO 2006048246 and DE 202004018245 of the applicant of the present invention, the published content of which shall also be treated as accompanying the present invention. The first reference publishes a device for wound treatment that resorts to a partial vacuum, where the device consists of an airtight wound cover, which, when placed on the body of the patient, forms a cavity between the wound in question and the wound cover device, with at least one port emanating from the cavity by which the air in the cavity may be evacuated, where the wound cover device is underlain by at least one area-covering wound care article that absorbs the wound secretions, where the volume of the article increases during the progression of the absorption process, such that the absorbed wound secretions are contained within the wound care article and thus beneath the wound cover device until the wound care article is removed from the body of the patient, where the wound care article has at least one layer of a textile segment augmented with superabsorbent material surrounded by a shell permeable to liquids, where the layer has an area measured as the extent of its flat side that is 3% to 90% smaller than the shell, such that the cross section of the wound care article will approach a circular shape as the wound care article approaches its maximum fill capacity.

The second publication listed describes a multi-component dressing using a partial vacuum for the treatment of a wound in a human or animal body that includes a wound cover component to be attached to skin or mucous membranes, at least one port emanating from the cavity above the wound by which materials present in the wound cavity may be evacuated, where the same includes superabsorbent polymers that absorb and bind the absorbed wound secretions until their removal from the wound cavity, where the absorption capacity of the polymers provide mutual synergies with the sub-atmospheric pressure.

The last publication listed describes a drainage device for treatment of wounds using a partial vacuum with an air-tight wound cover component made of a foil-like material that is adhesively attached to the body of the patient on the skin surface surrounding the wound area with an air-tight cavity between the wound and the wound cover component, with at least one drainage tube that may be inserted into the cavity and by which the materials present in the wound cavity may be evacuated, and with at least one wound care article to absorb wound secretions within the cavity, where the wound care article has at least one layer of a textile segment augmented with superabsorbent material surrounded by a shell permeable to liquids, where the absorbed wound secretions remain within the wound care article and thus below the wound cover component until the wound care article is removed from the body of the patient, and where the wound cover component has a treatment opening that may be closed air-tight and by which the wound care article may be inserted and removed from the cavity.

Moreover, the wound care article of the invention may be conformed to the anatomical features. For example, it may be designed as a cuff to be pushed onto an arm or a leg or a joint or as a bandage to be conformed to a heel or an elbow or the like.

The wound care article may also be designed to fit around a surgically implanted tube. Thus, the wound care article may have at least one slit such that the dressing may be applied on the body of the patient to fit around a tube (such as a drain tube or a catheter), where the wound care article will be associated with a second wound care article, which is also flat and which is applied at a distance from the first wound care article, where the distance between them will be bridged by a connecting strip. Such a wound care article is known, for example, from DE 202006005966 of the applicant of the present application, the content of which shall be included in full with the published content of the present description.

Likewise, it is preferable in this connection to design the wound care article to include at least one agent that could stop bleeding or a coagulation deficiency. Said agent may consist of at least one chemically and/or physiologically active agent or combination of agents or at least one physically active agent. Such a wound care article is known, for example, from a simultaneously submitted application of the applicant of the present application.

To this end, the wound care article may be embodied, for example:
- as an essentially flat segment of material incorporating absorbent material, which contains an absorbent fleece containing superabsorbent polymers and at least one chemically and/or physiologically active agent or combination of agents,
- as or in combination with a pressure or compression dressing,
- as a combination of a primary wound cover, which is not absorbent or only negligibly absorbent, which contains at least one chemically and/or physiologically active agent or combination of agents, and a secondary wound cover, which is peripheral to the primary cover, where the second cover contains superabsorbent polymers, with an optional diffusion barrier between the two covers,
- as a dressing bundle containing a primary wound cover with at least one chemically and/or physiologically active agent or combination of agents and a dressing segment placed on top of the wound cover, where at least portions of the segment contain superabsorbent polymers, and/or
- as a longitudinal segment of material, where the segment is elastically deformable and where the segment of material contains superabsorbent polymers and optionally at least one chemically and/or physiologically active agent or combination of agents.

It is preferable that the chemically and/or physiologically active agent or combination of agents contain at least one agent or a combination with styptic properties. Such agents are known under the category "styptics" and/or "haemostatics".

The physically active agent may be, for example, a tourniquet, a pressure pad, a pressure dressing or a compression dressing.

Other embodiments of the wound care article of the invention are designed such that
- the absorbent body (1; 11; 21) within the shell contains Airlaid material with hydroactive, preferably superabsorbent polymers as powders or granules, while the shell contains hydroactive, preferably superabsorbent polymers as fibers; both shell and absorbent body (1; 11; 21) within the shell contain Airlaid material incorporating hydroactive, preferably superabsorbent polymers;
- the shell consists of foam, and the absorbent body (1; 11; 21) within the shell contains Airlaid material incorporating hydroactive, preferably superabsorbent polymers;
- both shell and absorbent body (1; 11; 21) within the shell contain Airlaid material incorporating hydroactive, preferably superabsorbent polymers; and/or
- absorbent body (1; 11; 21) within the shell contains Airlaid material incorporating superabsorbent polymers as powders or granules, while the shell contains superabsorbent polymers as fibers.

It is particularly advantageous to design the article such that at least one component of the wound care article is movable relative to at least one other component of the wound care article.

This embodiment may be designed to have the absorbent body move loosely within the interior of the shell.

Alternatively, it may be designed such that all components of the wound care article are fixed in position relative to each other, thus such that they cannot move relative to each other. This may be achieved by gluing, welding, stitching or the like or by having the absorbent body of the same size as the shell, such that friction effects preclude movement that would otherwise be present.

A further embodiment designs the shell in the form of a pocket that is open on at least one side and that may have an optional closure. Said shell can then house an absorbent body in accordance with the invention, where the absorbent body may be selected to match its absorption properties to the wound characteristics.

A further advantageous embodiment provides for a shell in the form of a pocket open on one side with an airtight layer in at least one segment as well as a device to connect a vacuum device.

In this embodiment, the wound care article may be used for a partial vacuum therapy on a hand, a foot, an arm, a leg or the like. Such a partial vacuum therapy is indicated specifically for burns, which tend to have significant rates of exudation.

In this process, the shell of the wound care article may have a cuff near its opening into which the hand, for example, may be inserted and which will then facilitate an airtight fit. The device to connect a vacuum may consist of a stud transecting the shell to which the vacuum hose may be attached. Likewise, the device to connect a vacuum may also be integrated into said cuff such that a vacuum hose may be inserted here.

DEFINITIONS

The term "wound care article" shall refer in the following specifically to a wound cover, preferably a flat wound cover or a wound care cloth. Said wound cover may be absorbent just as well as not absorbent or only slightly absorbent. In particular, the term "wound care article" may also be understood as an aggregation of various products, which are combined in a specific arrangement on the wound to be treated. The arrangement may form a physical unit, where the various products are combined in a common shell or they may be connected by glue, possibly without a shell. However, the arrangement may also be provided as a kit, which combines the various articles with the assistance of a bandage in the desired arrangement on the wound to be treated.

The term "chronic wounds" shall refer to wounds that were not primarily caused by traumatic events. Admittedly, traumatic events may have been the original trigger for such a wound, but the chronic wound is characterized by a slower speed of the wound healing process. Chronic wounds may often have slight bleeding, if any, but may often be subject to copious exudation.

FIGURES

Figure 2:
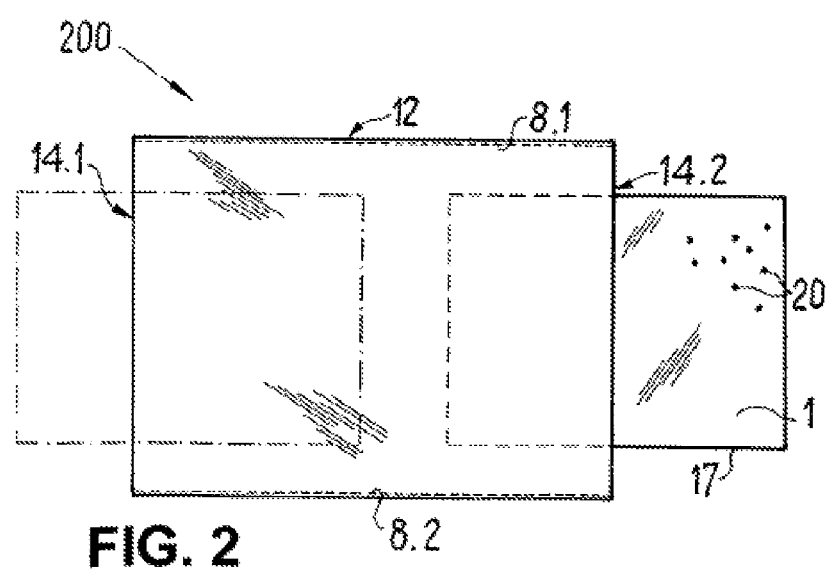
Figure 3:
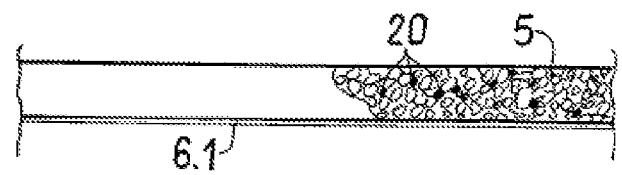
Figure 4:
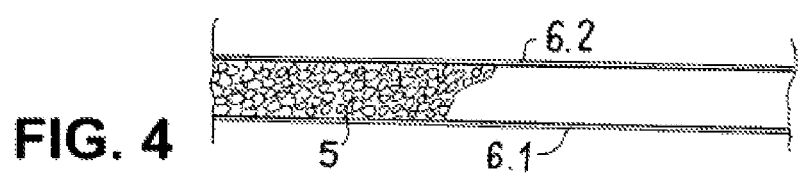
Figure 5:
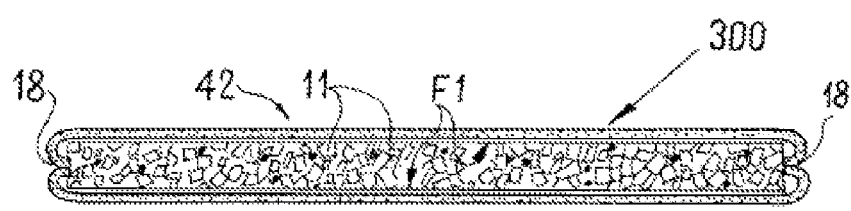
Figure 6:
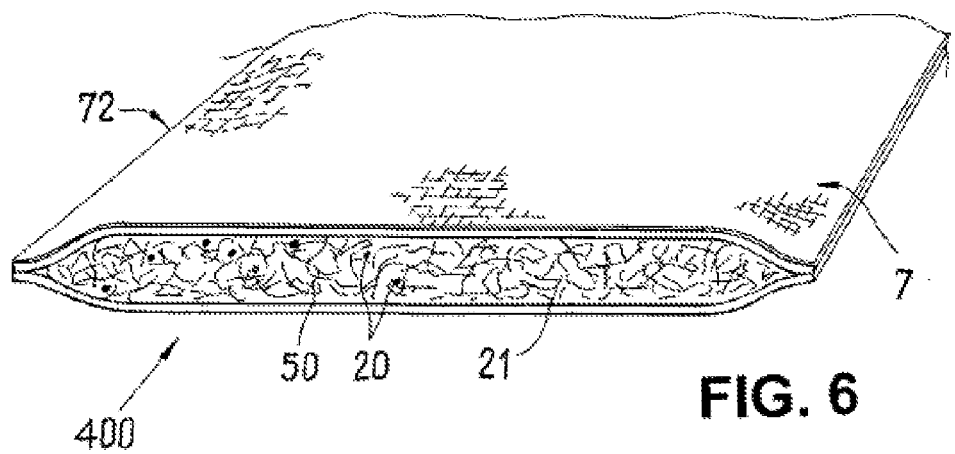
Figure 7:
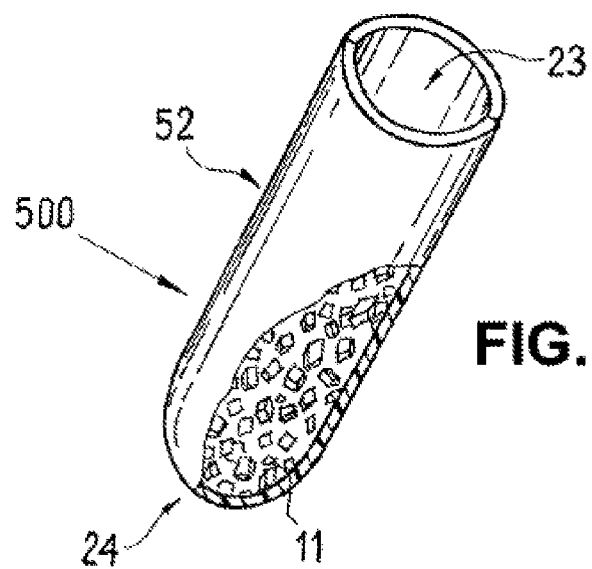
Figure 8:
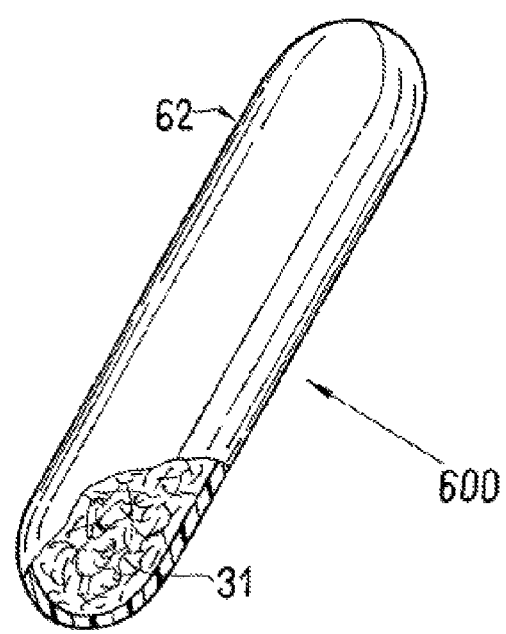
Figure 9:
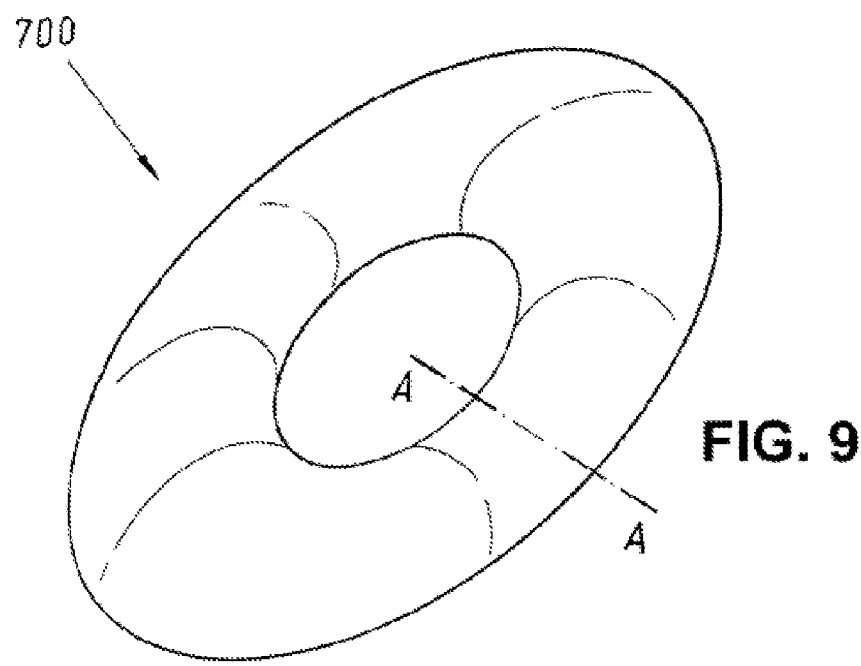
Figure 10:
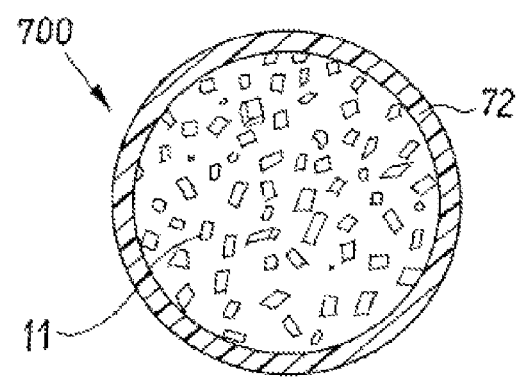
Figure 11:
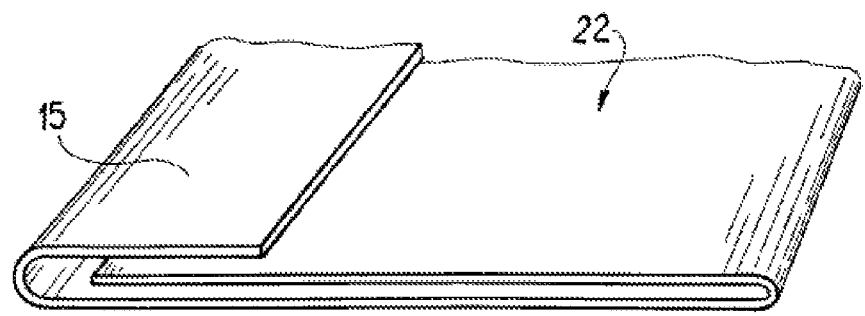
Figure 12:
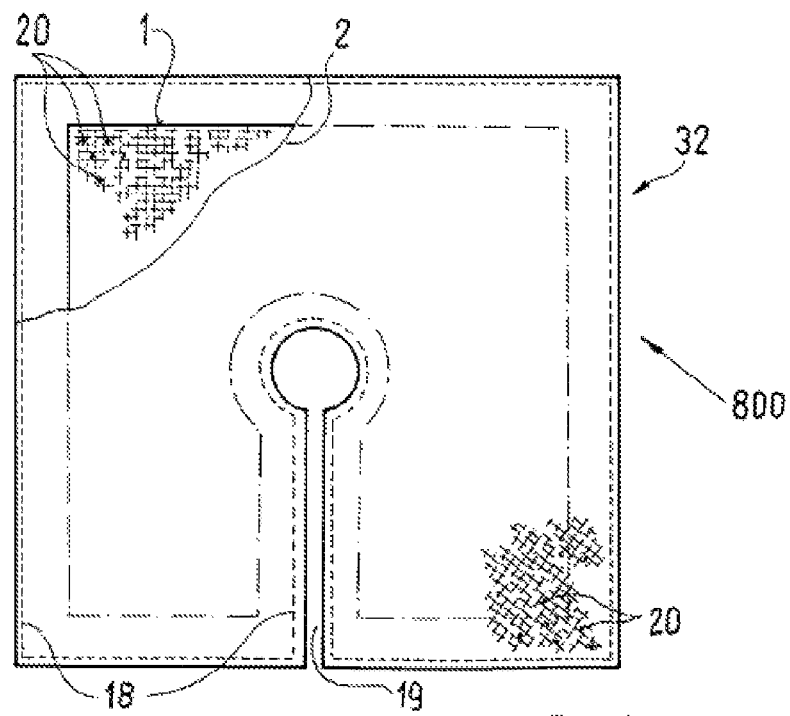
Figure 13:
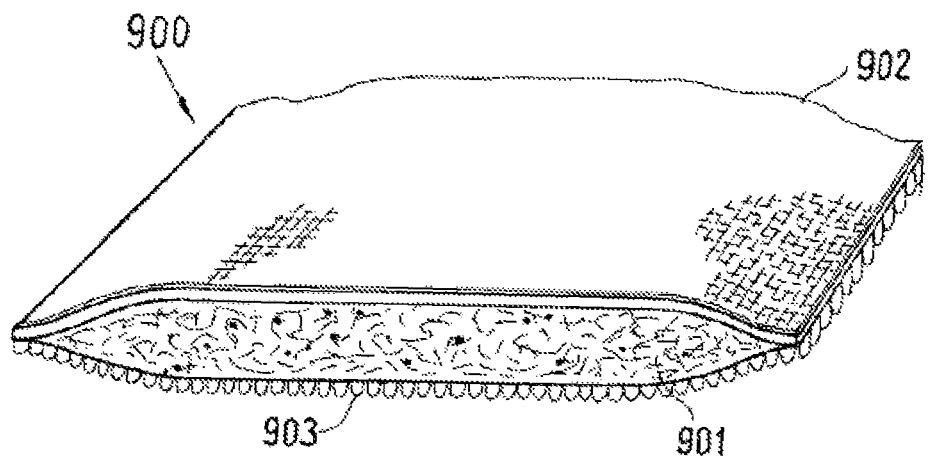
Figure 14:
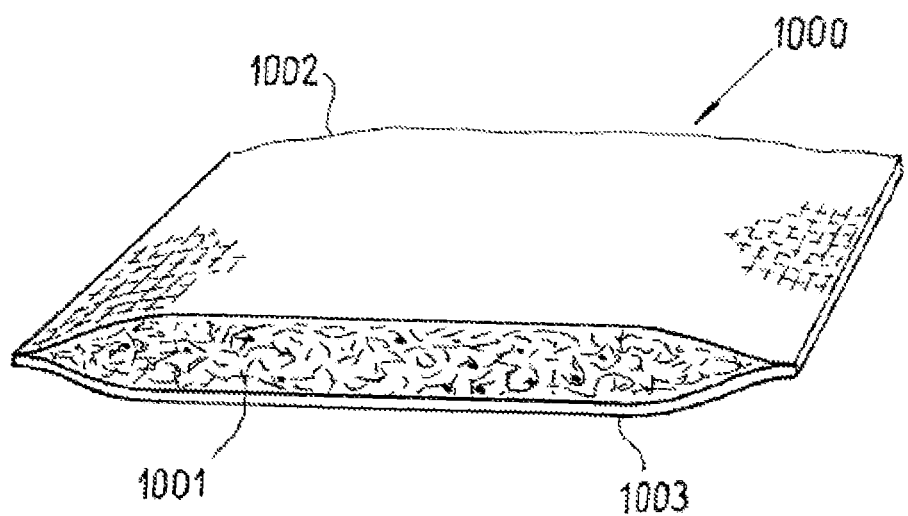
Figure 15:
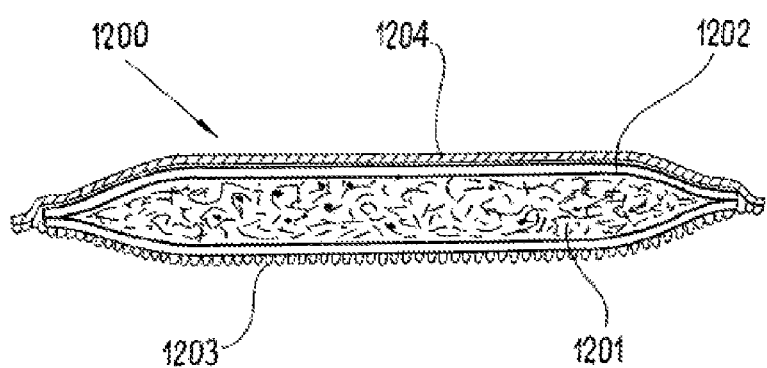

The resent invention will be explained in more detail by the Figures and examples shown and discussed in the following. It should be noted that the Figures and examples have only a descriptive character and are not intended to limit the invention in any manner. The Figures show:

FIG. 1 a flat wound care article in a side view;

FIG. 2 another flat wound care article, open on both sides, in a schematic top view of its flat side;

FIG. 3 a schematic cross section of foam-like shell material with a covering layer that is glued on;

FIG. 4 a schematic cross section of the foam-like shell material with covering layers glued onto both sides;

FIG. 5 a schematic cross section of another embodiment of the flat wound care article, where the shell is crimped over;

FIG. 6 a side view of a flat wound care article similar to FIG. 1, but with fiber fill;

FIG. 7 a side view of an essentially cylindrical wound care article intended for wound pockets;

FIG. 8 a side view of another wound care article intended for deep wounds, such as cavities;

FIG. 9 a side view of a ring-shaped wound care article;

FIG. 10 a cross section A-A in FIG. 9;

FIG. 11 a schematic side view of a shell with a closure flap;

FIG. 12 a slit compress in a top view of its flat side;

FIG. 13-15 show other embodiments of a wound care article of the invention.

FIG. 1 depicts a flat rectangular wound care article 100 consisting of body 1 to absorb the wound exudates, where body 1 is embodied as a mat containing cellulose, and of shell 2 surrounding the mat. Reference numbers 2.1 and 2.2 designate walls of the shell. Shell 2 and body 1 within shell 2 consist in the present case of known Airlaid mats containing the known powdery superabsorbent substance 20. Shell walls 2.1, 2.2 are linked by a circumferential seam 18. Wound care article 100 described here has an overall thickness of 4 mm to 5 mm.

FIG. 2 depicts wound care article 200, which is very similar to the above description, except that its shell 12 has only two opposite seams 8.1, 8.2, i.e. it has two open sides 14.1, 14.2 for the insertion of mat-like body 1. Given that the mat contains the powdery superabsorbent substance 20, it is necessary to seal the mat along its periphery 17.

As depicted in FIG. 3, the shell material consists of a soft foam layer 5 of polyurethane and a cover layer 6.1 consisting of very thin polyester foil that is glued onto the foam layer. Foam layer 5 contains also an amount of powdery superabsorbent substance 20.

FIG. 4 shows the sandwich-like structure of the shell material with the difference that foam layer 5 is covered on both sides by cover layers 6.1 and 6.2. Cover layers 6.1 and 6.2 are firmly attached to foam layer 5 across their entire extent.

FIG. 5 likewise presents a flat wound care article 300. This includes shell 42 generated by a reversal of shell 12 shown in FIG. 2. However, the foam-like shell material with a cover layer described for FIG. 3 was selected for shell 42. Of course, at least one of the sides (see FIG. 2) is open. The cover layer forms an interior surface F1 in the finished shell 42. Shell 42 houses an absorbent body 11 consisting of an aggregation of small cubed pieces of material with a size ranging from 1.5 mm to 4.0 mm, which were cut from the Airlaid mat or a waste product of the manufacturing process of the mat. Such an embodiment requires the provision of a finishing seam.

FIG. 6 shows a further wound care article (reference number 400), consisting of a flat shell 72 and a body 21 formed of multiple carboxymethylcellulose fibers 50. Carboxymethylcellulose fibers 50 are covered by a powdery superabsorbent substance 20, which adheres to the fibers. In another embodiment not shown here, the fibrous absorbent body consists exclusively of a superabsorbent substance.

Shell 22 shown in FIG. 11 has a closing clasp 15, which facilitates the insertion of a selected absorbent body, such as an aggregation of cubed alginate pieces or a mat, as needed into the interior of the shell.

A slit 19 made in rectangular wound care article 100 shown in FIG. 1 generates wound care article 800 in the form of a novel slit dressing with increased absorption capacity. Circumferential seam 18 extends into the slit.

FIG. 7 depicts wound care article 500 designed for deep wounds and cavities, which consists of a partly cylindrical shell 52 and the previously described absorbent body 11 embodied as an aggregation of small cubed pieces of material with a size of 2.0 mm to 4.0 mm covered by powdery superabsorbent substance 20. Shell 52 consists of soft polyurethane foam 3 mm thick. The pieces of material are generated by machine cutting of an Airlaid mat 2 mm thick. As shown in the Figure, shell 52 is open at one of its ends 23 and is rounded and closed at its second, opposite end 24.

Wound care article 600 shown in FIG. 8 has a geometrically very similar, but closed shell 62 with two rounded ends. The interior of shell 62 contains absorbent body 31 embodied as fibrous fill. The fill is loose and airy. As a consequence, the sausage-like wound care article 600 is especially well suited for wound healing in the anal area.

Finally, FIGS. 9 and 10 show a ring-like wound care article 700, where shell 72, which consists of polyurethane foam, has a circular cross section, as is shown in FIG. 10. The interior (absorbent body 11) consists of the same cubed pieces of material described for FIG. 7. There is nothing to preclude incorporating a radial slit (not depicted here) into wound care article 700 in order to generate a ring-like slit dressing.

FIG. 13 shows a wound care article 900 with body 901 to absorb wound exudates and a composite overall shell, where the liquid-absorbing shell forms the upper side 902 (furthest from the wound) of the overall shell and the shell incapable of absorbing liquids forms the lower side 903 (closest to the wound) of the overall shell. Shell 903, which is incapable of absorbing liquids, is a wound spacing screen.

FIG. 14 shows wound care article 1000 with absorbent body 1001 to absorb wound exudates and with a composite overall shell, where the shell incapable of absorbing liquids is the upper surface 1002 (furthest from the wound) of the composite shell and the absorbent shell is the lower surface 1003 (closest to the wound) of the composite shell. Shell 1002, which is incapable of absorbing liquids, protects the clothing from getting soiled.

FIG. 15 shows wound care article 1200 with body 1201 to absorb wound exudates and an absorbent shell 1202 surrounded by a composite outer shell, of which the lower surface 1203 (closest to the wound) serves as a wound spacing screen, whereas the upper surface 1204 (furthest from the wound) protects the clothing from getting soiled.

The invention claimed is:

1. A wound care article, comprising an absorbent body that is adapted to absorb wound liquids, and an outer shell including only two walls that surround the absorbent body, wherein the two walls of the outer shell are linked to form an open or closed hollow body and each of the two walls includes superabsorbent polymers and a soft foam that can absorb liquids, wherein the outer shell is adapted to absorb wound liquids, and the absorbent body fits within an interior of the outer shell.

2. The wound care article of claim 1, wherein the wound care article is flat prior to use.

3. The wound care article of claim 1, wherein the outer shell further includes wool, cotton, natural sponge, or carboxymethylcellulose.

4. The wound care article of claim 1, wherein the soft foam is a polyurethane foam.

5. The wound care article of claim 1, wherein the absorbent body further includes superabsorbent polymers.

6. The wound care article of claim 5, wherein the superabsorbent polymers are granules, powders, aggregations, compressed material, foam, fibers, woven fiber, fiber mats, fiber fleece or fiber padding.

7. The wound care article of claim 1, wherein the outer shell further includes nutritional additives or antibiotics for topical application in the wound healing process.

8. The wound care article of claim 1, wherein the absorbent body contains an airlaid material that includes hydroactive polymers in powder or granulate form and the outer shell further includes hydroactive polymers in fiber form.

9. The wound care article of claim 1, wherein the absorbent body contains an airlaid material that includes hydroactive polymers.

10. The wound care article of claim 9, wherein the hydroactive polymers are superabsorbent polymers.

11. The wound care article of claim 8, wherein the hydroactive polymers in powder or granulate form and the hydroactive polymers in fiber form are superabsorbent polymers.

12. A method for absorbing wound liquids, comprising placing the wound care article of claim 1 on a wound and applying compression to the wound care article.

13. A method for absorbing wound liquids, comprising placing the wound care article of claim 1 on a wound and applying a partial vacuum to the wound care article.

14. A wound care article for advancing the healing of chronically exudating wounds, the wound care article comprising an absorbent body and an outer shell including only two walls, wherein the outer shell surrounds the absorbent body, the absorbent body is adapted to absorb wound liquid, the outer shell is adapted to absorb wound liquid, and the two walls of the outer shell are linked to form an open or closed hollow body and each of the two walls includes superabsorbent polymers and a soft foam that can absorb liquids.

15. The wound care article of claim 1, wherein the material of the outer shell is supplied in a sandwich structure.

16. The wound care article of claim 15, wherein the sandwich structure contains at least one foam layer and at least one foil-like or web-like cover layer.

17. The wound care article of claim 16, wherein the cover layer is pleated or crinkled.

18. The wound care article of claim 15, wherein the sandwich structure is an airlaid mat with perforated cover.

19. The wound care article of claim 18, wherein the perforated cover is flexible.

20. The wound care article of claim 1, wherein the outer shell consists of highly absorbent material with an absorption potential for wound exudates that is at least triple a weight of the highly absorbent material.

21. The wound care article of claim 14, wherein the material of the outer shell is supplied in a sandwich structure.

22. The wound care article of claim 14, wherein the outer shell consists of highly absorbent material with an absorption potential for wound exudates that at least triples the weight of the material.

23. The wound care article of claim 19, wherein the flexible cover is pleated or crinkled.

* * * * *